(12) United States Patent
Adjouadi et al.

(10) Patent No.: US 10,137,308 B2
(45) Date of Patent: Nov. 27, 2018

(54) ELECTROCARDIOGRAPHY TRIGGERED TRANSCRANIAL MAGNETIC STIMULATION SYSTEMS AND METHODS OF USING THE SAME

(71) Applicant: THE FLORIDA INTERNATIONAL UNIVERSITY BOARD OF TRUSTEES, Miami, FL (US)

(72) Inventors: Malek Adjouadi, Miami, FL (US); Mercedes Cabrerizo, Miami, FL (US); Niovi Rojas, Miami, FL (US); Juan Omar Perez, Miami, FL (US); Jesus de la Rua, Miami, FL (US); Anastasio A. Cabrera, Parrish, FL (US)

(73) Assignee: The Florida International University Board of Trustees, Miami, FL (US)

( * ) Notice: Subject to any disclaimer, the term of this patent is extended or adjusted under 35 U.S.C. 154(b) by 494 days.

(21) Appl. No.: 14/777,256

(22) PCT Filed: Mar. 17, 2014

(86) PCT No.: PCT/US2014/030681
§ 371 (c)(1),
(2) Date: Sep. 15, 2015

(87) PCT Pub. No.: WO2014/145847
PCT Pub. Date: Sep. 18, 2014

(65) Prior Publication Data
US 2016/0038754 A1 Feb. 11, 2016

Related U.S. Application Data

(60) Provisional application No. 61/798,170, filed on Mar. 15, 2013.

(51) Int. Cl.
*A61N 2/00* (2006.01)
*A61B 5/0402* (2006.01)
*A61B 5/00* (2006.01)

(52) U.S. Cl.
CPC ............ *A61N 2/006* (2013.01); *A61B 5/0402* (2013.01); *A61B 5/4064* (2013.01);
(Continued)

(58) Field of Classification Search
CPC .... A61N 2/006; A61B 5/0402; A61B 5/4064; A61B 5/4836; A61B 5/486; A61B 5/4088
See application file for complete search history.

(56) References Cited

U.S. PATENT DOCUMENTS 5,769,778 A 6/1998 Abrams et al.
6,117,066 A * 9/2000 Abrams .................. A61N 1/08
128/897

(Continued)

OTHER PUBLICATIONS

International Search Report and Written Opinion, dated Aug. 28, 2014, PCT/ISA/210, PCT/ISA/220, PCT/ISA/237.

*Primary Examiner* — Kaylee Wilson
(74) *Attorney, Agent, or Firm* — Saliwanchik, Lloyd & Eisenschenk

(57) ABSTRACT

Systems that integrate electrocardiography (ECG) functions and Transcranial Magnetic Stimulation (TMS) functions, as well as methods of manufacturing such systems and methods of performing ECG and TMS using such systems, are provided. A system can include a hardware component and a software component in operable communication with the hardware component. The hardware component can include or be in operable communication with a TMS machine, and the software component can be configured to receive waveforms from ECG hardware.

12 Claims, 9 Drawing Sheets

(52) U.S. Cl.
CPC .......... *A61B 5/4836* (2013.01); *A61B 5/4088* (2013.01); *A61B 5/486* (2013.01)

(56) References Cited

U.S. PATENT DOCUMENTS

| | | |
|---|---|---|
| 2005/0261542 A1 | 11/2005 | Riehl |
| 2006/0122675 A1 | 6/2006 | Libbus et al. |
| 2009/0036938 A1 | 2/2009 | Shipley et al. |
| 2009/0083070 A1* | 3/2009 | Giftakis ............. A61N 1/36132 705/2 |
| 2011/0207988 A1* | 8/2011 | Ruohonen ................ A61B 5/05 600/9 |
| 2012/0197089 A1 | 8/2012 | Svojanovsky |
| 2013/0158422 A1* | 6/2013 | Zhang .................. A61B 5/0464 600/516 |

* cited by examiner

Neuro-navigated Transcranial
Brain Stimulation Machine
(TMS)
↓
Simultaneous TMS and EEG
Evaluation
↓

Integrating ECG and TMS into
a Cardiovascular TMS System
(CTS)
↓
CTS – Hardware Elements
↓

Complete System:
Hardware Component
and Software Module
linking ports of a
Computing Device as
a Graphical Interface
↓
Integrating the
Hardware design of
the CTS with a
Computing Device
which embeds the
software as a
Graphical User
Interface (GUI)
↓

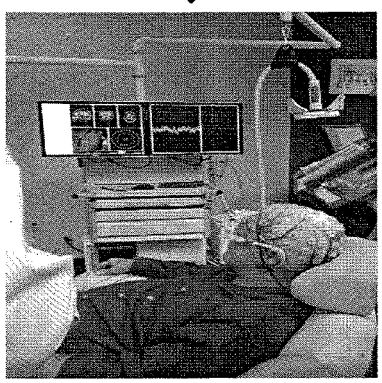
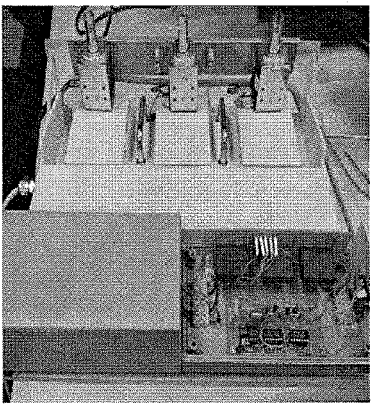

← Electronic
Components of the
CTS design

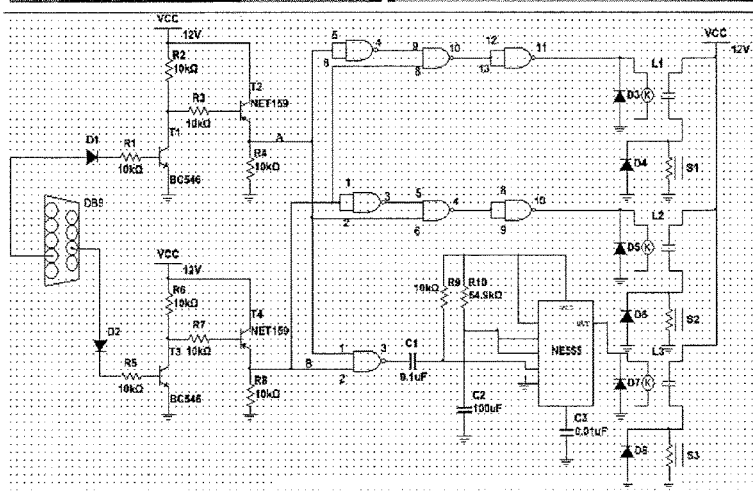

FIG. 1

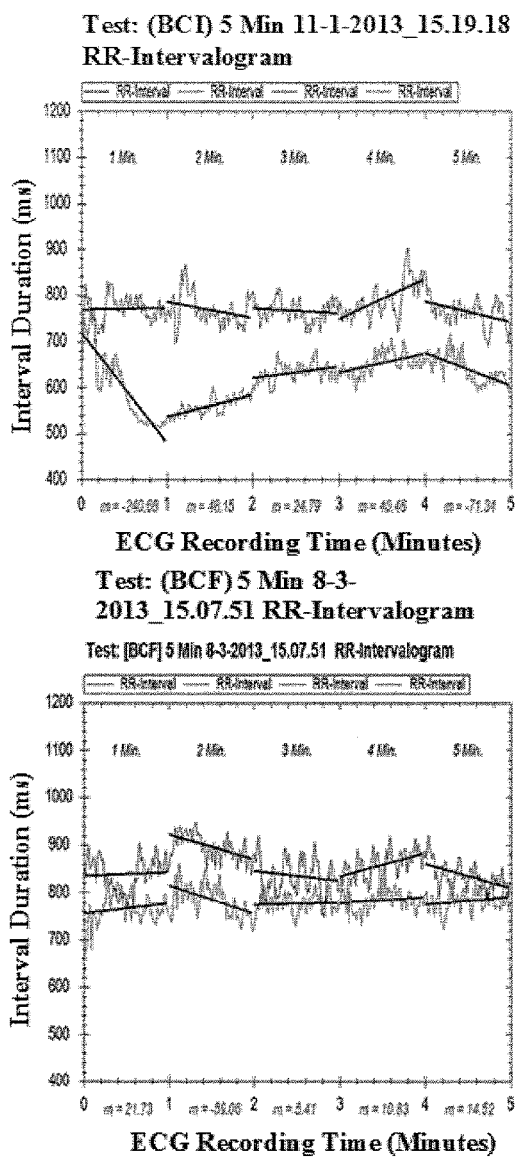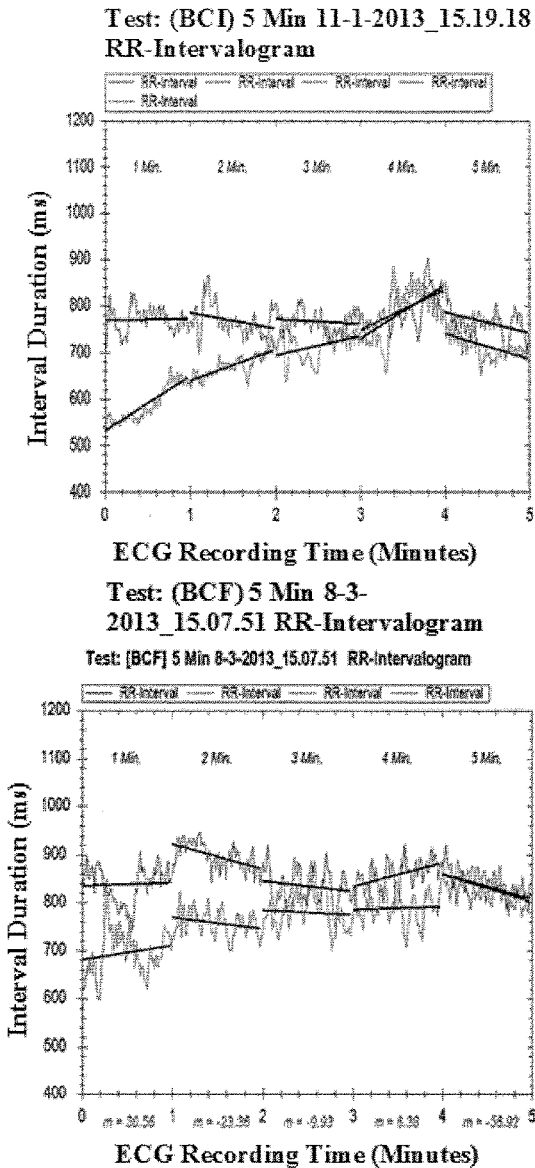
FIG. 9

ELECTROCARDIOGRAPHY TRIGGERED TRANSCRANIAL MAGNETIC STIMULATION SYSTEMS AND METHODS OF USING THE SAME

CROSS-REFERENCE TO RELATED APPLICATIONS

This application is a national stage application of International Patent Application No. PCT/US2014/030681, filed Mar. 17, 2014, which claims the benefit of U.S. Provisional Patent Application Ser. No. 61/798,170, filed Mar. 15, 2013, each of which is hereby incorporated by reference herein in its entirety, including any figures, tables, and drawings.

GOVERNMENT SUPPORT

The subject invention was made with government support under a research project supported by National Science Foundation Award No. CNS-0959985. The government has certain rights in this invention.

BACKGROUND OF INVENTION

Electrocardiography (ECG; also referred to in the industry as "EKG") devices are used for obtaining waveforms corresponding to cardiac activity in a patient. Transcranial Magnetic Stimulation (TMS) machines are used to apply magnetic stimulation to the head area of a patient. Slowing of a patient's heart rate can lead to many severe health problems, especially for patients who may already suffer from a condition that affects the heart.

BRIEF SUMMARY

Embodiments of the subject invention provide hardware-software assimilated systems that align, in time and space, electrocardiography (ECG) with the neuro-navigated Transcranial Magnetic Stimulation (TMS) (e.g., a TMS machine), as well as methods of manufacturing such systems and methods of performing ECG and TMS using such systems. A system of the present invention can be integrated and non-invasive and can include a hardware component that can automatically activate pedals of the TMS machine to, for example, perform different operational functions, including increasing intensity of the magnetic pulse, decreasing intensity of the magnetic pulse, providing a magnetic pulse with a predefined intensity, and aborting the stimulation if any undue effect on the cardiac rhythm is detected. The system can also include a software component, stored on one or more computer-readable media (e.g., non-transitory media), that can serve a dual purpose of: reading an ECG signal and synchronizing the trigger of the TMS machine via the hardware component, a synchronization which can be made in relation to any of the deflections of the recorded ECG (e.g., in order to maintain a normal heartbeat during stimulation); and serving as a graphical user interface (GUI) for a user of the system.

Embodiments of the subject invention provide an integrated Cardiovascular-TMS System (CTS) that can control magnetic stimulation of the brain according to selected moments of the cardiac cycle, as well as methods of manufacturing such systems, methods for integrating the ECG and TMS functionalities, and methods of performing ECG and TMS using such systems. If magnetic stimulus from a TMS machine is not adequately synchronized with the cardiac cycle, there is potential for slowing the heart rate, but the same stimulus can produce minimal or no alteration of the heart rate if an adequate synchronization is carefully chosen. Systems and methods of the subject invention can ensure the latter result. Systems of the subject invention can provide a new understanding on how information flow is best synchronized between ECG and TMS in both directions, as well as affirm the necessary precautions needed to be considered by doctors, technical staff, and clinicians when performing brain magnetic stimulation (e.g., single pulse or repetitive) in a wide range of applications. Applications for the systems and methods of the subject invention include, but are not limited to, performing brain mapping of the eloquent cortex for pre-surgical evaluations, administering stimulations for treatment related to depression, Alzheimer's disease and other memory disorders, migraine headaches, autism, attention deficit hyperactivity disorder (ADHD), attention deficit disorder (ADD), and other applications currently performed in clinical centers and medical establishments involving the use of magnetic stimulation.

In one embodiment, a system includes: a hardware component having an integrated circuit; and a software component stored on a non-transitory computer-readable medium and in operable communication with the hardware component. The integrated circuit is in operable communication with a TMS machine, and the software component is configured to receive waveforms from electrocardiography (ECG) hardware. The software component is also configured to compute a determination factor based on the waveforms and, if the determination factor is outside a predetermined range, send an abort signal to the TMS machine such that the TMS machine ceases any magnetic stimulation.

In another embodiment, a method for controlling magnetic stimulation to a patient includes: determining the current state of a patient's heart; and controlling magnetic stimulation to the patient based on the heart state determination. The controlling can include providing a control signal that controls the generation of or level of magnetic stimulation provided by a TMS machine. The controlling can further include preventing or inhibiting any magnetic stimulation by the TMS machine if it is determined that a conditionality factor (also referred to as a determination factor) of the patient's heart falls outside a predetermined normal range.

BRIEF DESCRIPTION OF THE DRAWINGS

FIG. 1 is a block diagram of a cardiovascular Transcranial Magnetic Stimulation (TMS) system (CTS) according to an embodiment of the subject invention.

FIG. 9 is an illustration of observed changes on RR intervals for two subjects: subject 1 (top row); and subject 2 (bottom row).

DETAILED DISCLOSURE

Figure 2:
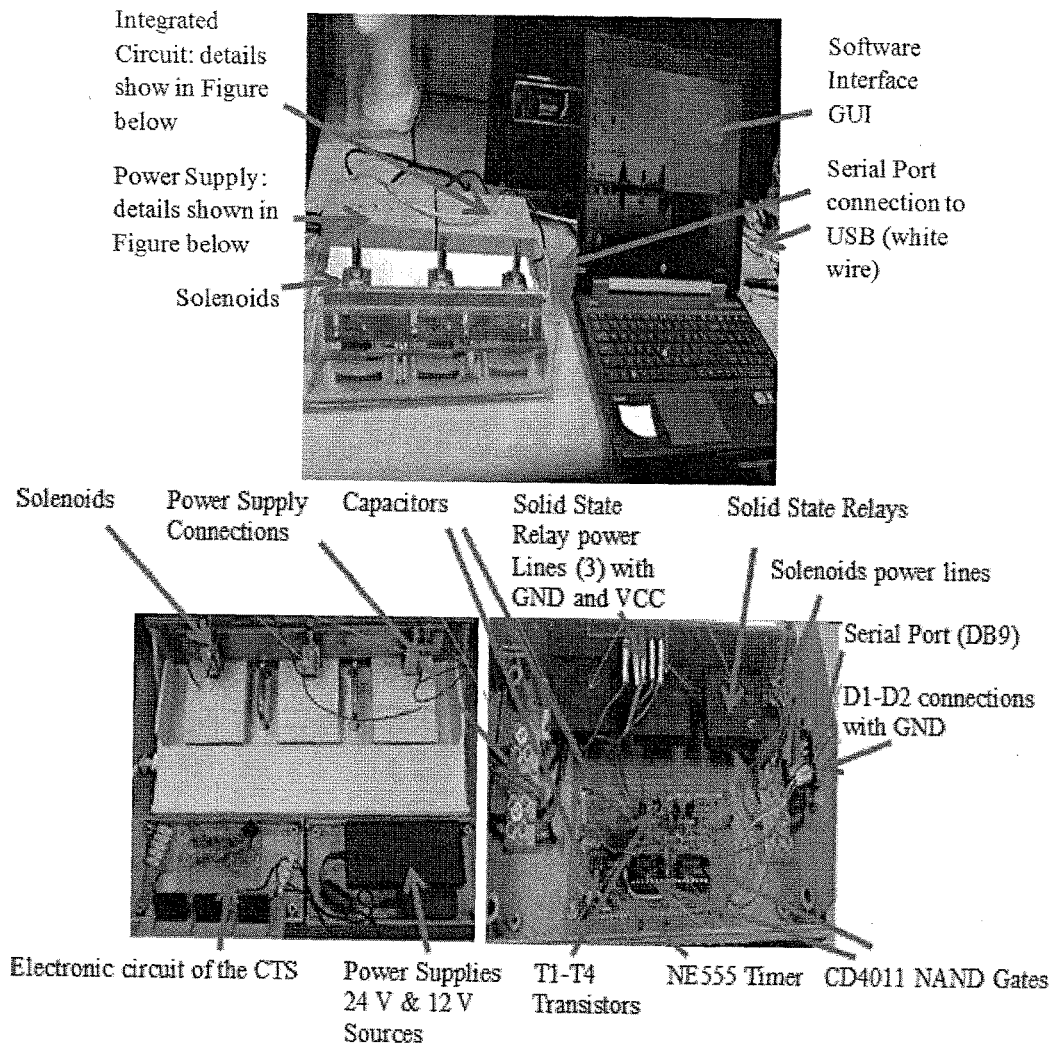
FIG. 2 is a diagram of components of a CTS according to an embodiment of the subject invention.

When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

Embodiments of the subject invention include a hardware-software integrated design that aligns in time and space electrocardiography (ECG) with a neuro-navigated Transcranial Magnetic Stimulation (TMS) machine. Time and space alignment refer to the opportunity for simultaneous recordings of the ECG under repeated transcranial magnetic stimulation while using the same 3D coordinate system on a same patient. This integrated and non-invasive system can include the following two fully-adapted components: (i) a novel hardware design solution that can automatically activate solenoids of TMS pedals for different operational functions (e.g., for four different operational functions); and (ii) a novel software module. In an embodiment, the hardware design solution can activate solenoids of TMS pedals for the following four different operational functions: (1) increase intensity of the magnetic pulse; (2) decrease intensity of the magnetic pulse; (3) trigger the electromagnetic pulse with a predefined intensity of the pulse; and (4) abort stimulation (e.g., if any undue effects are seen in the ECG signal). In an embodiment, the software module can serve the following two purposes: (1) read the ECG signal and synchronizes the trigger of the TMS via the hardware component, a synchronization which can be made in relation to specific patient-based deflections of the recorded ECG in order to maintain a normal heartbeat during stimulation; and (2) serve as a graphical user interface for user-machine interaction.

Embodiments of the subject invention provide hardware-software assimilated systems that align, in time and space, electrocardiography (ECG) with the neuro-navigated Transcranial Magnetic Stimulation (TMS) (e.g., a TMS machine), as well as methods of manufacturing such systems, methods for integrating the ECG and TMS functionalities, and methods of performing ECG and TMS using such systems. A system of the present invention can be integrated and non-invasive system and can include a hardware component that can automatically activate pedals of the TMS machine to, for example, perform different operational functions, including increasing intensity, decreasing intensity, and triggering a magnetic pulse. The system can also include a software component, stored on one or more computer-readable media (e.g., non-transitory media), that can serve a dual purpose of: reading an ECG signal and synchronizing the trigger of the TMS machine via the hardware component, a synchronization which can be made in relation to any of the deflections of the recorded ECG (e.g., in order to maintain a normal heartbeat during stimulation); and serving as a graphical user interface (GUI) for a user of the system.

Embodiments of the subject invention provide integrated Cardiovascular TMS Systems (CTSs) that can control magnetic stimulation of the brain according to selected moments of the cardiac cycle), as well as methods of manufacturing such systems and methods of performing ECG and TMS using such systems. If magnetic stimulus from a TMS machine is not adequately synchronized with the cardiac cycle, there is potential for slowing the heart rate, but the same stimulus can produce minimal or no alteration of the heart rate if an adequate synchronization is carefully chosen. Systems of the subject invention can ensure the latter result. Systems of the subject invention can provide a new understanding on how information flow is best synchronized between ECG and TMS in both directions, as well as affirm the necessary precautions needed to be considered by doctors, technical staff, and clinicians when performing brain magnetic stimulation (e.g., single pulse or repetitive) in a wide range of applications. Applications for the systems and method of the subject invention include, but are not limited to, performing brain mapping of the eloquent cortex for pre-surgical evaluations, administering stimulations for treatment related to depression, Alzheimer's disease, other memory disorders, migraine headaches, autism, attention deficit hyperactivity disorder (ADHD), attention deficit disorder (ADD), and other applications currently performed in clinical centers and medical establishments.

FIG. 1 is a block diagram for a CTS according to an embodiment of the subject invention. Referring to FIG. 1, the CTS system includes a hardware component and a software component, which can be stored on one or more computer-readable media (e.g., non-transitory media). One or more connections can be provided to connect the hardware component and the software component. The hardware component and the software component can be configured to send signals to each other and receive signals from each other.

In many embodiments, the hardware component includes a hardware circuit, such as an integrated circuit, having one or more circuit elements (e.g., resistors, diodes, transistors, capacitors, relays, NAND gates, timers, solenoids). A hardware circuit can be operably connected to a TMS machine and/or ECG hardware. The hardware circuit can receive signals from the software component and relay them to the TMS machine and/or the ECG hardware to perform the desired functions and can receive signals from the TMS machine and/or the ECG hardware and relay them to the software component. In a further embodiment, the ECG hardware and/or the TMS machine can be considered part of the hardware component. The ECG hardware can include typical ECG components known in the art.

Figure 3:
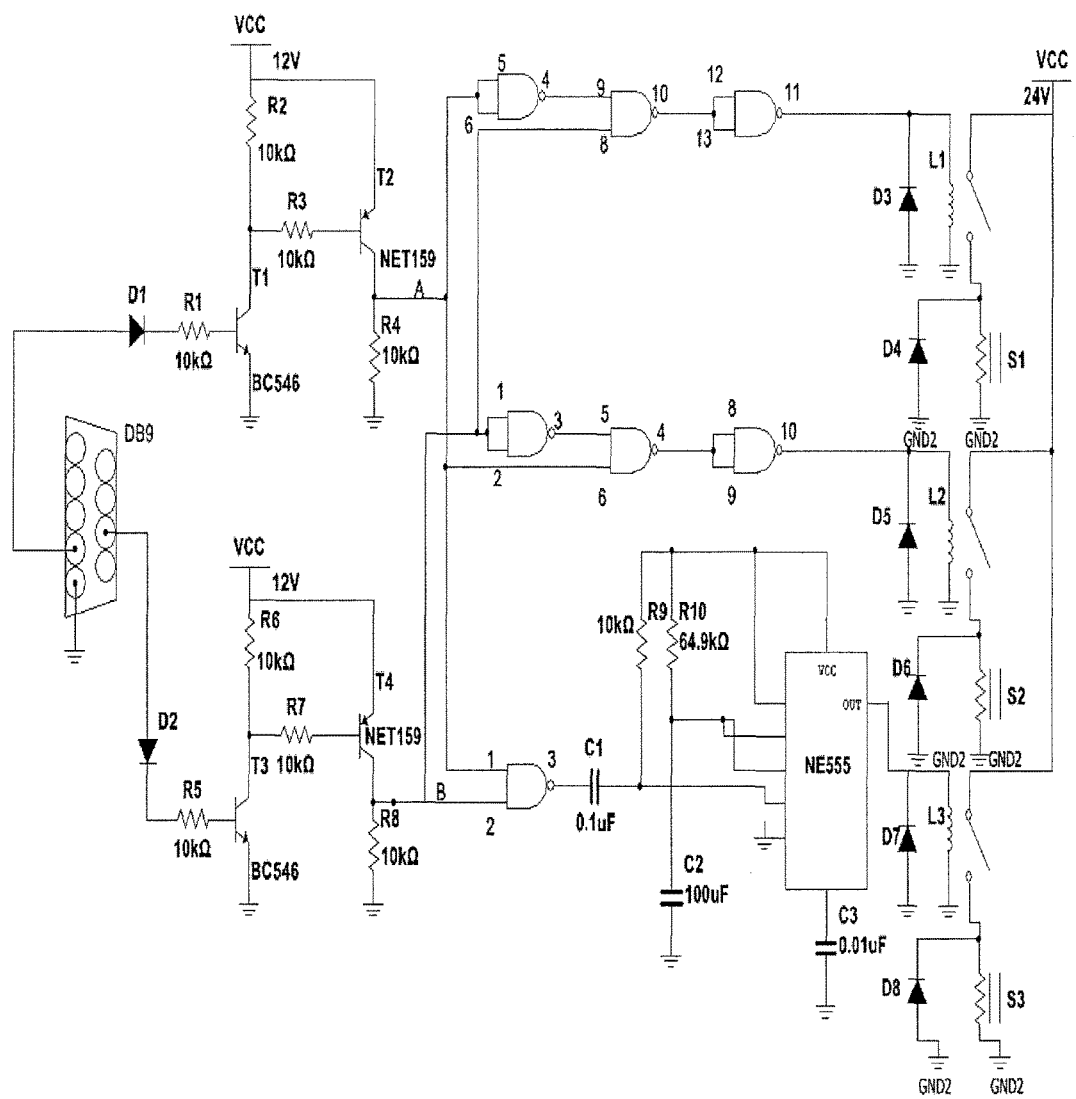
FIG. 3 is a schematic of a hardware circuit according to an embodiment of the subject invention.

FIG. 3 shows a schematic of a hardware circuit according to an embodiment of the subject invention. Referring to FIG. 3, in one embodiment, a hardware circuit includes NAND gates (e.g., CMOS NAND gates), solenoids, diodes (e.g., eight diodes), transistors (NPN and PNP transistors), a timer, solid state relays (SSRs), capacitors, and resistors. Quad 2-input NAND gates can be used and can provide binary output (e.g., to control pedals of a TMS machine). The solenoids can be 24 V DC intermittent solenoids. Diodes D1, D2 can be used to rectify the signal coming from the serial port, such that only positive values will be used as input to the transistors. Additional diodes D3-D8 can be used as inputs to the SSRs and the solenoids to protect the inductors of these components from feedback current. NPN transistors T1, T3 and PNP transistors T2, T4 can be used to, for example, change the output voltage from diodes D1, D2 to the desired input voltage (e.g., 12 V or 0 V to the NAND gates). The timer can be used as a precision timing device for the automatic pushing and releasing of the solenoids as a function of the NAND gate outputs. The SSRs can control the large voltage that would activate the appropriate solenoid by providing it with the appropriate electric current. Two capacitors can be connected to the timer in order to filter out the noise coming from the power supply. An additional capacitor can be provided and combined with a resistor (e.g., a 64.9 kΩ resistor) to provide the necessary delay needed for the timer to send a signal to the relay to close the switch and activate solenoid 3 to trigger the magnetic pulse. These values provided on FIG. 3 are for exemplary purposes only, and embodiments are not limited thereto.

In many embodiments, the hardware circuit automates the functionality of the pedals intrinsic to a TMS machine in order to provide all the controls for increasing intensity, decreasing intensity, and triggering a magnetic pulse. The higher the intensity of the TMS machine, the deeper is the area of the brain that can be stimulated.

In one embodiment, the hardware component includes a TMS machine and may optionally include ECG hardware. The software component communicates (i.e., sends signals to and receives signals from) directly with the TMS hardware and/or the ECG hardware.

In certain embodiments, the TMS machine includes pedals. The pedals can be used to increase the intensity of the TMS machine, decrease the intensity of the TMS machine, and trigger a magnetic pulse of the TMS machine. The TMS machine can include, for example, three or more pedals, though embodiments are not limited thereto. For example, the TMS machine can include three pedals, and each pedal can perform one function out of: increasing the intensity; decreasing the intensity; and triggering a magnetic pulse. In a further embodiment, the TMS machine or the hardware circuit of the CTS includes one or more solenoids. The solenoids can be used to control the pedals, and one solenoid can be present for each pedal. For example, the TMS machine can include three pedals, and a first solenoid can trigger a first pedal which increases the intensity, a second solenoid can trigger a second pedal which decreases the intensity, and a third solenoid can trigger a third pedal which triggers a magnetic pulse. It should be noted that although solenoids were used to control the existing pedals from a commercially available TMS machines, as will be discussed further below, in one embodiment of the invention, control signals can be provided to the TMS machine controller that will cause a TMS pulse to be generated, TMS pulse to be increased in intensity, or TMS pulse to be decreased in intensity by the TMS machine without the need for pedals as currently being done in a manual fashion. The control signals can also be controlled based on cardiac activity in order to provide the patient a much safer experience when being subjected to TMS therapy.

The software component can include a software module stored on one or more computer-readable media (e.g., non-transitory media). The software component can be stored on, for example, a compact disc (CD), digital video disc (DVD), flash memory device, volatile memory, or a hard disk drive (HDD), such as an external HDD or the HDD of a computing device.

In many embodiments, the software component is used via a computing device, and the software is either stored on a portion of the computing device (e.g., HDD or volatile memory) or is on a computer-readable medium being read by the computing device. A computing device can be, for example, a laptop computer, desktop computer, server, a cell phone, or tablet, though embodiments are not limited thereto. A user can operate the software component through a GUI of the software component, which allows the user to interact with the software via the computing device. In one embodiment, the software is a closed-source C Sharp (C#) programming software module. The GUI of the software component can be configured to allow a user to set which deflection of the heart is best suited for brain stimulation.

In one embodiment, the software component is stored on a laptop computer, tablet, or desktop computer. In a particular embodiment, the software component is stored on a laptop computer.

In many embodiments, the software component is specifically designed and configured to interact with the hardware component and to allow a user to operate the hardware component through the GUI of the software component. A user can operate a TMS machine of the hardware component to, for example, increase the intensity, decrease the intensity, trigger a magnetic pulse, cease (abort) the stimulation function, turn the TMS machine on, or turn the TMS machine off. Similarly, a user can operate ECG hardware to perform any type of ECG recording using all the leads available (e.g., all twelve leads) or a subset of them, for example, ceasing function, turning on, and turning off the ECG recording system. These functions can be accomplished, for example, by the user entering a command through the GUI which the software component then relays to the hardware component. Such a command can be input by, for example, using a computing device which has the software component stored thereon or is reading the computer-readable medium having the software component to input the command. The software component then transmits a signal to the hardware component (e.g., to the hardware circuit, the TMS machine, and/or the ECG hardware) to perform the input function.

The software component also receives signals from the hardware component to, for example, monitor the ECG results of a patient.

In one embodiment, the software component is configured to relay a command for increasing the intensity, decreasing the intensity, or triggering a magnetic pulse of a TMS machine by sending a signal to depress pedals of the TMS machine. The pedals can be depressed, thereby causing the TMS machine to perform the desired function. Such signals can be sent to solenoids to trigger the pedals. In an alternative embodiment, the software component is configured to send signals directly to the processing center of the TMS machine (either through the hardware circuit or not) to cause it to increase the intensity, decrease the intensity, trigger a magnetic pulse, cease function, turn the TMS machine on, or turn the TMS machine off.

In many embodiments, the software component is configured to relay a command to ECG hardware by sending a signal to the ECG hardware. Such signals can be sent directly to the processing center of the ECG hardware (either through the hardware circuit or not). Also, the software component can be configured to receive signals from the ECG hardware and save the signals to the computer-readable medium on which the software component is stored or to a computer-readable medium with which the software component is in operable communication. The signals can be saved in any suitable format, for example, ASCII format.

In many embodiments, the software module of the software component is configured to acquire and analyze ECG data in real time and automatically issue the appropriate control signals for the selection of the TMS mode of operation.

The software component and the hardware component can be connected to each other through connection between the hardware component and a computing device, the computing device either having the software portion stored thereon or being in operable communication with a computer-readable medium on which the software portion is stored. The hardware component and the computing device can be connected to each other using any suitable means known in the art. For example, the hardware component and the computing device can be connected to each other using wires (e.g., universal serial bus (USB) wires, serial wires, fire wire, etc.) or through wireless communication (e.g., through a wireless network and/or using a wireless transmitter and wireless receiver), though embodiments are not limited thereto. If using wires, such wires can connect to the hardware component and/or the computing device using ports provided thereon, including but not limited to, USB ports, serials ports, and fire wire ports. In one embodiment, such a computing device can be considered to be part of the software component.

In many embodiments, the software component is configured to automatically abort any TMS stimulation, any ECG procedure, or both, if a determination factor falls outside a predetermined normal range. The software component is configured to receive signals from the hardware component and computes (e.g., periodically or continuously) multiple values to monitor any TMS stimulation and/or ECG procedure. One or more determination factors can be set ahead of time by a user, as can acceptable (or normal) ranges for each determination factor. If a determination factor falls outside the normal range, the software component automatically sends a signal to the TMS stimulation machine (either through the hardware circuit or not), the ECG hardware (either through the hardware circuit or not), or both, to abort. Such an abort can include shutting off and/or ceasing function. In a further embodiment, such an abort can include simply decreasing intensity.

A PQRST waveform of an ECG can provide several clinical indicators. A normal ECG can include a P wave, a QRS complex, and a T wave, collectively known as a PQRST waveform. The P wave represents atrial depolarization, the QRS complex represents ventricular depolarization, and the T wave reflects the phase of rapid repolarization of the ventricles. The P wave is the first wave of the electrocardiogram and represents the spread of electrical impulse through the atrial musculature (activation or depolarization). The QRS complex represents the spread of the electrical impulse through the ventricular muscle (depolarization), and is made up of the Q wave, the R wave, and the S wave. The first deflection, if it is negative (downward), is labeled the Q wave. The first positive (upward) deflection is labeled the R wave, whether it is preceded by a Q wave or not. A negative deflection following an R wave is labeled an S wave. The T wave represents the period of recovery for the ventricles (repolarization). Generally, the direction, shape, and magnitude of the T wave are considered.

The interval from the peak of an R wave in one QRS complex to the peak of the R wave in the next QRS complex is called an RR interval (also referred to as an inter-beat interval). The interval between the beginning of the P wave and the beginning of the QRS complex of an electrocardiogram, representing the time between the beginning of the contraction of the atria and the beginning of the contraction of the ventricles, is called a PR interval. The distance between the first point of the downward slope of the Q wave and the highest point of the upward slope of the S wave is called the length of the QRS complex (or QRS duration). The time from the beginning of the Q wave to the end of the T wave, representing the duration of ventricular electrical activity, is called the QT interval. Because ECG signals could be affected by noise, and since the R-wave peak is the highest in the QRS complex, in an embodiment, the RR is the interval of choice for monitoring the effects of TMS on the cardiac rhythm.

Figure 4:
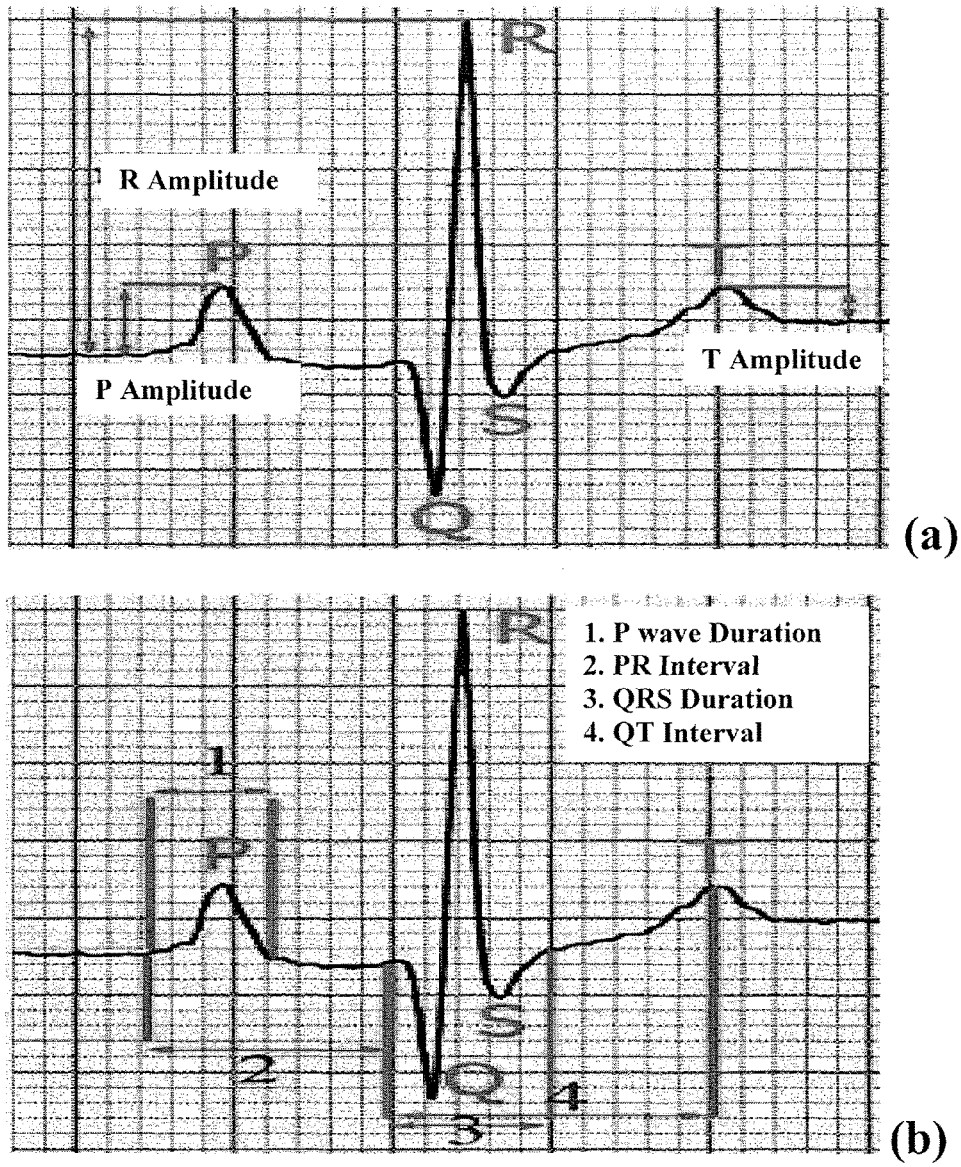
FIGS. 4a and 4b are PQRST waveforms from an electrocardiography device.

FIGS. 4a and 4b show PQRST waveforms. Referring to FIG. 4a, each wave (P, Q, R, S, and T) is labeled, and notations show how the amplitudes of the P wave, the R wave, and T wave are measured. Referring to FIG. 4b, notations show how a P wave duration 1, a PR interval 2, a QRS duration 3, and QT interval 4 are measured.

In many embodiments of the subject invention, a TMS stimulation can be aborted when an unforeseen event is recorded (e.g., a determination factor is outside a normal range), and such an unforeseen event can be tied to any perturbation in the PQRST waveform. A perturbation can be a change over the baseline that is deemed significant, for example, such a change can be in a value of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, or more. The change in percent over the baseline can be set differently for healthy controls but with a reduced tolerance (smaller percentage) for subjects with heart ailments and under clinical supervision. An event that leads to the software component automatically aborting a TMS stimulation can be a perturbation of any component of the PQRST waveform, even if the focus is on the RR interval, which can be captured more accurately. Such a perturbation could be a perturbation in the duration, magnitude, shape, or direction of any portion of the PQRST waveform over the baseline. For example, the duration of the RR interval can be used, such that if the RR interval is computed to be outside of a predetermined normal range (e.g., 0.6 seconds to 1 the software component automatically aborts the TMS stimulation. A QT interval can be corrected with respect to variations observed in the RR interval, i.e., the faster the heartbeat, the smaller the QT interval would be. Unduly prolonged or unduly shortened QT intervals could signify a risk for ventricular arrhythmia. Thus, in a particular embodiment, the length of the QT interval can be used as a factor that, if abnormal, can cause the TMS stimulation to be aborted (i.e., an unduly long or short QT interval can be an unforeseen event that can cause the TMS stimulation to be aborted). This aborted TMS stimulation can be accomplished by a control signal being generated that causes the TMS machine to stop providing TMS pulses.

A normal rhythm of the heart (also called a normal sinus rhythm) can include an RR interval between 0.6 sec (equivalent to 100 beats per minute or bpm) and 1 sec (60 bpm) or between about 0.6 seconds (sec) and 1 sec. A normal sinus rhythm can also include a PR interval between 0.12 sec and 0.20 sec or between about 0.12 sec and about 0.20 sec. A normal sinus rhythm can also include a QRS complex length of less than 0.12 sec, 0.12 sec or less, or less than about 0.12 sec. A normal sinus rhythm can also include a 1:1 ratio of P wave to QRS complex, such that a P wave is present for each QRS complex.

In one embodiment, a TMS stimulation can be aborted if the duration of the RR interval is computed to be outside a predetermined normal range (e.g., 0.6 sec to 1 sec, or about 0.6 sec to about 1 sec).

Though the RR interval and QT interval have been given as examples of factors that can be used to determine whether a TMS stimulation is to be aborted, any aspect of the PQRST waveform(s) can be used, depending on the patient and the input of the user. The software component can be easily reconfigured on a patient-by-patient basis to consider any potential deviation away from any range of measurements for any characteristic of any aspect of the PQRST waveform (s). That is, not only can a user determine which characteristic of which aspect of the PQRST waveform(s) to use as a determining factor to abort a TMS stimulation, the acceptable or normal range for that characteristic for that aspect of the PQRST waveform(s) can also be changed.

Also, though exemplary ranges and values have been given for various aspects of a PQRST waveform, embodiments are not limited thereto. According to embodiments of the subject invention, acceptable values or ranges for determination factors can be set or changed by a user at any time, before or during operation. Thus, one or more determination factors and acceptable values and ranges for those determination factors can be set on a patient-by-patient basis.

In certain embodiments of the subject invention, a CTS allows synchronization to be achieved with the highest peak of the R wave. The software component detects the maximum peak of the R wave(s) automatically based on signals received from the hardware component, and a trigger for brain stimulation is automatically initiated once this peak is detected. The part of the R wave from which brain stimulation is triggered can be, for example, the start of the R wave, the peak of the R wave, or the start of the descent from the peak. In one embodiment, the part of the R wave from which brain stimulation is triggered is the maximum peak of the R wave. Use of the R wave of the ECG (early depolarization of the ventricles) is advantageous because it is easy to detect, has the highest amplitude of all the PQRST deflections, and is the least likely to affect the normal electrical activity of the heart. The interval between any two adjacent R peaks (RR interval) can be calculated accurately by the software component based on signals received from the hardware component. The RR interval measurement is very useful in gauging the ventricular rate. In various embodiments, the software component is configured to detect the P wave peak or the PP interval (to accurately determine the atrial rate), in addition to or alternative to any other elements the software component can detect, as discussed herein.

In one embodiment, a method of manufacturing a CTS includes providing a software component as described herein to a computing device and connecting the computing device to a hardware component as described herein. Providing the software component to the computing device can include installing the software component on the computing device (e.g., on an HDD of the computing device) or providing a computer-readable medium having the software component stored thereon to the computing device such that the computing device is in operable communication with the computer-readable medium.

In one embodiment, a method of performing ECG and TMS stimulation on a patient includes providing a CTS as described herein in operable communication with a TMS machine and ECG hardware connected to the patient, performing TMS stimulation on the patient, and monitoring PQRST waveforms of the patient provided by the ECG hardware. The waveforms can be monitored by the software component of the CTS and/or by a user interfacing with a GUI of the software component. The user can interface with the GUI using a computing device having the software component stored thereon or in operable communication with a computer-readable medium having the software component stored thereon. If a determination factor, based on the PQRST waveforms, falls outside an acceptable range, the software component automatically aborts the TMS stimulation. The user can adjust the determination factor(s) and the acceptable range for each determination factor at any time. Also, the user can manually increase the intensity, decrease the intensity, or trigger a magnetic pulse of the TMS machine using the GUI.

Embodiments of the subject invention advantageously provide easy and automated control of a TMS machine using a GUI. ECG output can be monitored to adjust the TMS machine accordingly. An automatic abort function can be provided within the software module to abort TMS stimulation if a determination factor moves outside an acceptable range, thereby providing enhanced safety for the patient.

Embodiments of the subject invention also allow for safe and easy evaluation of the effects of brain stimulation on the electrical activity of the brain. A TMS machine can be used for stimulation while waveforms from ECG hardware can be monitored for evaluation purposes and for safety purposes. An automatic abort function of the software module, as described herein, can provide further safety. The precise synchronization of the two modalities (brain stimulation and electrical activity analysis), according to embodiments of the subject invention, augments the capabilities and interpretation of TMS-induced changes to the cardiac system.

Additionally, embodiments of the present invention fully integrate brain stimulation with ECG. A CTS according to the subject invention is capable of performing in real time the following operations: (1) synchronization of the ECG with the TMS machine; (2) acquisition and analysis of the ECG; (3) artifact removal; (4) conversion of the saved ECG signal to ASCII format for compatibility with other interfaces; (5) correction of the R-wave peaks detected; (6) calculation and plotting of the extended standard ECG leads including the aVF, aVR, and aVL. The "a" stands for augmented, V is for voltage, R is for right arm, L is for left arm, and F is for left foot, all on the basis of the Einthoven's triangle configuration.

Further, embodiments of the present invention can have broad advantages for hospitals and research centers. New hypotheses can be tested and new interpretations of the TMS induced changes in the electrical activity of the heart can be considered, with the potential for new research findings and scientific insights. This unique approach, of the subject invention, at collecting data simultaneously across different recording modalities can help lead to a new understanding of the functional brain mappings in direct relation to the heart, and can help refine theoretical and design premises. Also, the increased knowledge of the human brain that will result from the subject technology can help promote scientific discovery while ensuring at all times the well-being of the patient.

Moreover, embodiments of the subject invention can also be used with spatially co-registered anatomical Magnetic Resonance Imaging (MRI), so that engineers, scientists, and clinicians can visualize and delineate functional mappings of the brain with high accuracy. Moreover, due to the integration of ECG with a TMS machine, precise analysis and interpretation of the ECG provide a more complete assessment of a given patient ensuring harmony between non-invasive brain stimulation through magnetic waves and the normal heart rhythm as observed in the ECG signal. Such a multimodal system allows for the appropriate timing for safe delivery of the brain stimulation, while continuously monitoring the ECG signal. The same mechanism which automates the different functions of the TMS can also abort the stimulation if any unwarranted effects are observed in the ECG. Many patients can benefit from the subject technology, including those with cardiac arrhythmias, metabolic disorders present in diabetic patients, neurological disorders, and ventricular repolarization abnormalities associated with a dispersion of the QT interval in the ECG waveform. In the latter case, the behavior of the deflections of the ECG in response to the magnetic brain stimulation can help predict early autonomic neuropathy affecting the autonomic nerves, which control the bladder and intestinal tract, among other organs.

In addition, embodiments of the subject invention advantageously allow for synchrony between any of the deflections observed in the ECG and the timing at which point brain stimulation can be given in the safest way possible, while continuously monitoring the electrical activity of the heart as observed in the ECG for any unforeseen effect, with the added ability of aborting the stimulation process if the latter case arises.

Further, embodiments of the subject invention allow for real time monitoring and diagnosis, based on the PQRST deflections of the entire ECG waveform. With this added real-time analysis, a wider spectrum of different scenarios can be observed on the electrical activity of the heart, in context to the administered brain stimulation, and can help promote study and lead to related diagnoses.

In some embodiments, the CTS including the graphical user interface that allows a user to control the CTS can be incorporated into a TMS machine so that the functionality provided by the CTS can be integrated and potential cost savings in manufacture can be attained.

In some embodiments, ECG or other heart related information can be inputted into the TMS with integrated CTS capability in order to control the TMS pulses as discussed above.

Although TMS stimulation has been discussed herein, other magnetic stimulation to a patient that might affect the patient's heart can also be controlled with embodiments of the invention.

The methods and processes described herein can be embodied as code and/or data. The software code and data described herein can be stored on one or more computer readable media, which may include be any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); or other media now known or later developed that is capable of storing computer-readable information/data. Computer-readable media should not be construed or interpreted to include any propagating signals.

EXAMPLES

Following are examples that illustrate embodiments and procedures for practicing the invention. These examples should not be construed as limiting.

Example 1

A CTS was manufactured. FIG. 2 shows hardware and software components of the CTS. The CTS was designed to interface with a TMS machine having three pedals as commercially available, one for increasing intensity, one for decreasing intensity, and one for triggering a magnetic pulse. The CTS was also designed to interface with ECG hardware such that PQRST waveforms are provided to the software component.

Referring to FIG. 2, the CTS has a software component installed on the HDD of a laptop computer and is connected via a USB cable to a port of the hardware component, which includes a hardware circuit. A circuit diagram of the hardware circuit is shown in FIG. 3. The circuit includes the following components:

CD4011—CMOS NAND gates: These are Quad 2-INPUT NAND GATE integrated circuits (IC) that provide the necessary binary output to automatically control the three pedals of a TMS machine. These NAND gates can generate the binary outputs that will automate the mode of operation of the TMS machine as shown in Table 1. The three binary outputs (01, 10, or 11) each trigger one of the three solenoids. The solenoid selected will in turn activate the respective pedal to increase intensity of the magnetic pulse (binary output 01), decrease intensity of the magnetic pulse (binary output 10), or trigger the magnetic pulse (single or repetitive; binary output 11).

5EGL9 SOLENOID INTERMITTENT 24 V DC: This is an electromechanically-operated valve with 24 DC coil volts and with intermittent duty cycle. The valve is controlled by an applied electric current. This element converts electrical energy into mechanical energy, which allows pushing or releasing the TMS pedal automatically. Depending on the output of these NAND gates, the intensity of the TMS machine can be increased (01), the intensity of the TMS machine can be decreased (10), or a magnetic pulse can be triggered (11).

IN3064 and NTE116-10 DIODES: Diodes D1 and D2 are used to rectify the signal coming from the serial port. Only positive values will be used as input to the transistors. The rectified signal coming from the serial port will go through these diodes to enter the transistors. Diodes D3-D8 are used as the inputs to the solid state relays (SSR) and the solenoids to protect the inductors of these components from feedback current. These components allow electrical current to flow in one direction and will inhibit any current passing in the opposite direction.

BC546 NPN and NET159 PNP TRANSISTORS: BC546 NPN transistors (T1 and T3) and NET159 PNP transistors (T2 and T4) are used to change the output voltage from diodes D1 and D2 to the desired input voltage 12 V or 0 V to the NAND gates.

NE555 TIMER: The NE555 timer is used as a precision timing device responsible for the automatic pushing and releasing of the solenoids as a function of the NAND gates outputs.

SSR HFS27 SOLID STATE RELAYS: These electronic switching devices control the large voltage that would activate the appropriate solenoid by providing it with the appropriate electric current.

CAPACITORS (0.1 µF, 0.01 µF): These capacitors are connected to the NE555 timer in order to filter out the noise coming from the power supply.

CAPACITOR (100 µF): This capacitor combined with a 64.9 kΩ resistor provides the necessary delay needed for the timer to send the signal (binary output 11) to the relay to close the switch and activate solenoid 3 to trigger the magnetic pulse.

The CTS was configured such that, TMS stimulation could be aborted if an RR interval of the PQRST waveform (s) was computed by the software component to be outside a range of 0.6 seconds to 1 second, inclusive.

TABLE 1

NAND GATE circuitry outputs to generate modes of operation of the TMS machine

| CD4011 Binary Output | Automated Mode of Operation for the TMS |
|---|---|
| 00 | Abort stimulation |
| 01 | Increase intensity of the magnetic pulse |
| 10 | Decrease intensity of the magnetic pulse |
| 11 | Trigger the magnetic pulse with a predefined intensity |

Example 2

Experiments were conducted in facilities on the campus of Florida International University using the CTS described in Example 1. Ten subjects were tested following a protocol defined as follows. The Nexstim's rTMS was employed in full integration with an ECG system, where the r in front of the TMS denotes the option for the more elaborate repetitive pulse stimulation process. An ECG device with 12 leads following the montage on the basis of the well-known Einthoven's triangle was utilized in order to record the frontal and precordial ECG activity. Twelve recording signals, 6 bipolar and 6 unipolar, were obtained. A 10-minute baseline before and after stimulation was recorded. Blood pressure was monitored throughout the entire experiment. Five-minute repetitive stimulation (SR=10 intensity=50% of the highest intensity reached by the coil) sequence was followed allowing for 5 stimulations and 5 1-minute interval of no stimulation. The motor cortex was stimulated using six electrode sites—F3, FC3, and C3 for the left hemisphere, and F4, FC4, and C4 for the right hemisphere—positioning the coil in the horizontal and tilted position using an angle of 30 degrees. Results were analyzed based on the RR interval (distance between heart beats) of the PQRST deflections of the ECG waveform(s).

Left side stimulation was found to be more effective than that of the right side for all subjects. Frontal electrode positions F3 and FC3 of the coil were more effective than the C3 location. The coil in the horizontal position was more effective than the tangential one. The left FC3 electrode location stimulation was immediately followed by an increase of the RR intervals (reduced heart rate, a rapid vagal effect) and thereafter by a progressive increase (acceleration, a delayed sympathetic effect) that lasted until the next stimulus was performed.

Preliminary studies on these 10 normal subjects from 20 to 30 years of age demonstrated that the Transcranial Magnetic Stimulation (TMS) can induce changes in the heart rhythm. The autonomic activity that controls the cardiac rhythm was indeed altered by an rTMS session targeting the motor cortex using an intensity based on the subject's motor threshold and lasting no more than 5 minutes.

Figure 5:
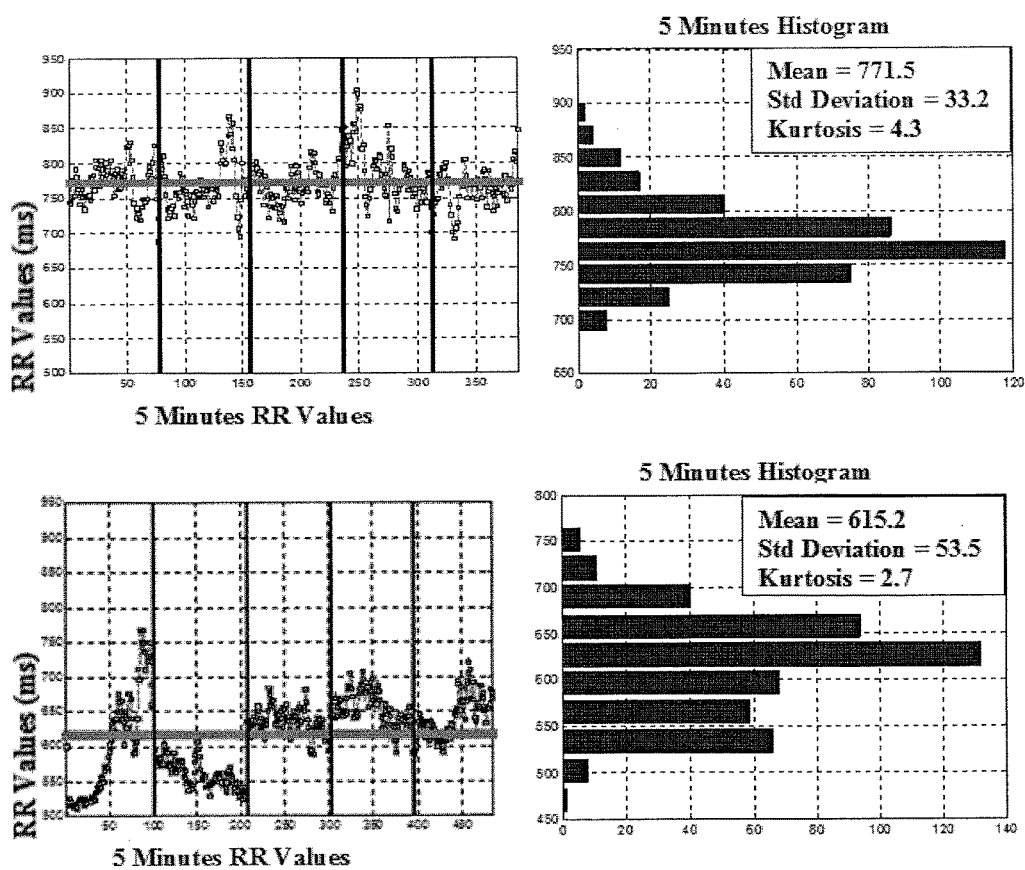
FIG. 5 shows RR interval and related histograms comparing (a) baseline to (b) active phase.

FIG. 5 shows RR interval and related histograms comparing (a) baseline to (b) active phase. Referring to FIG. 5, the heart rate variability (HRV) was significantly changed. An increase of the heart rate was noticed, as the RR interval values decreased due to the stimulation on the left frontal motor cortex. Specifically to this subject, during the first minute (vertical black lines divide the session into 5-minute increments), there was an evident decrease of the RR interval values when comparing the base line (subject at rest without stimulation) with what is referred to as "active" response when the subject is stimulated using rTMS.

As can be observed from the histograms of FIG. 5, the mean of the RR interval value dropped from 771 in the baseline to 615 during the stimulation phase. Furthermore, the standard deviation increased from 33.2 at baseline to 53.5 during stimulation.

Figure 6:
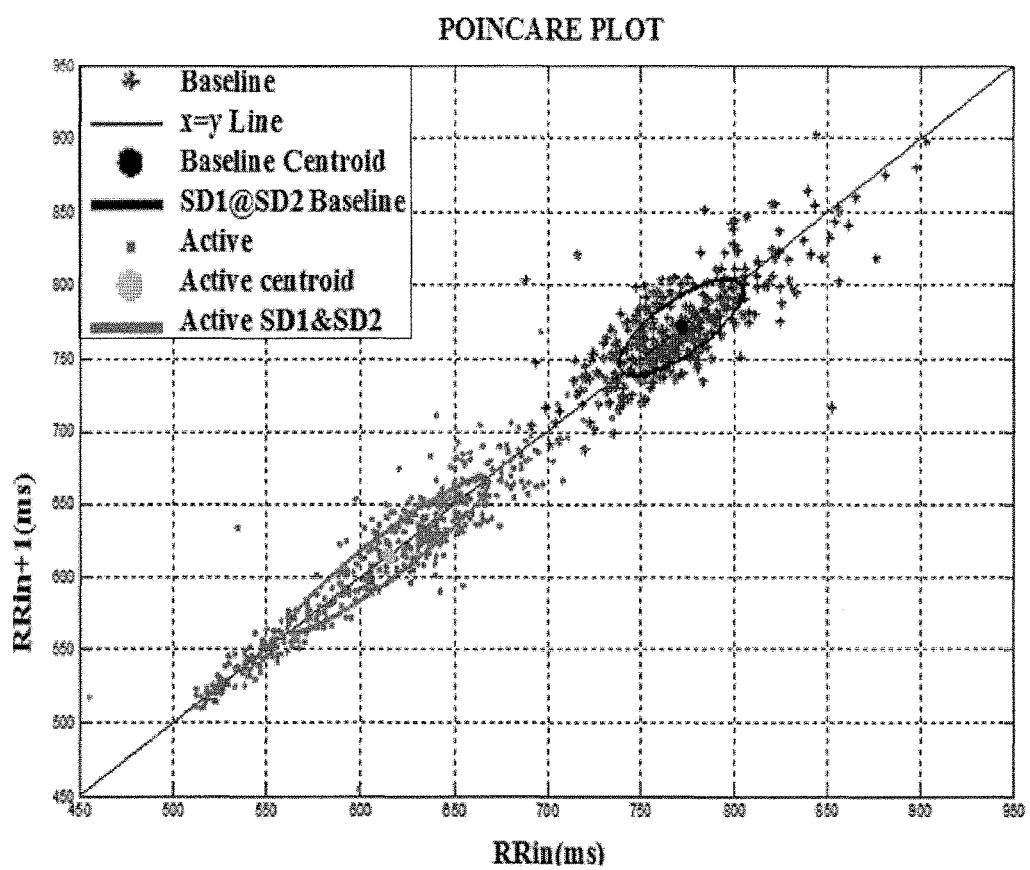
FIG. 6 is a Poincare plot of the distribution of RR intervals.

FIG. 6 shows a Poincare plot with the distribution of the RR interval values during baseline and with stimulation performed on the left side of the motor cortex. Referring to FIG. 6, a clear displacement and higher concentration of the points (i.e., shorter RR distances) is observed during stimulation as recorded from the F1L electrode, which is located on the left hemisphere. The line (x=y) in the plot has a physiological significance because all the points that fall in this line correspond to equal and consecutive RR interval values (distances from: R(1)-R(2), R(2)-R(3), and so on until R(n-1)-R(n)). All the points above the identity line correspond to a decrease in the heart rate and the points below this line correspond to an increase in the heart rate.

Indices from the HRV can be extracted in time and frequency domain. The distribution of the power spectral during the 5 minutes of ECG recording may vary with respect to changes in the autonomic modulation of the heart rate. In humans there are two frequency ranges of interest defined in the Low frequency (LF=0.04-0.15 Hz) and the High Frequency (HF=0.15-0.4 Hz). Parasympathetic and sympathetic effects are associated with the changes of these frequencies. Parasympathetic activity is considered responsible for these HF. Both parasympathetic and sympathetic activities, together with other mechanisms, are considered to determine LF [28].

Figure 7:
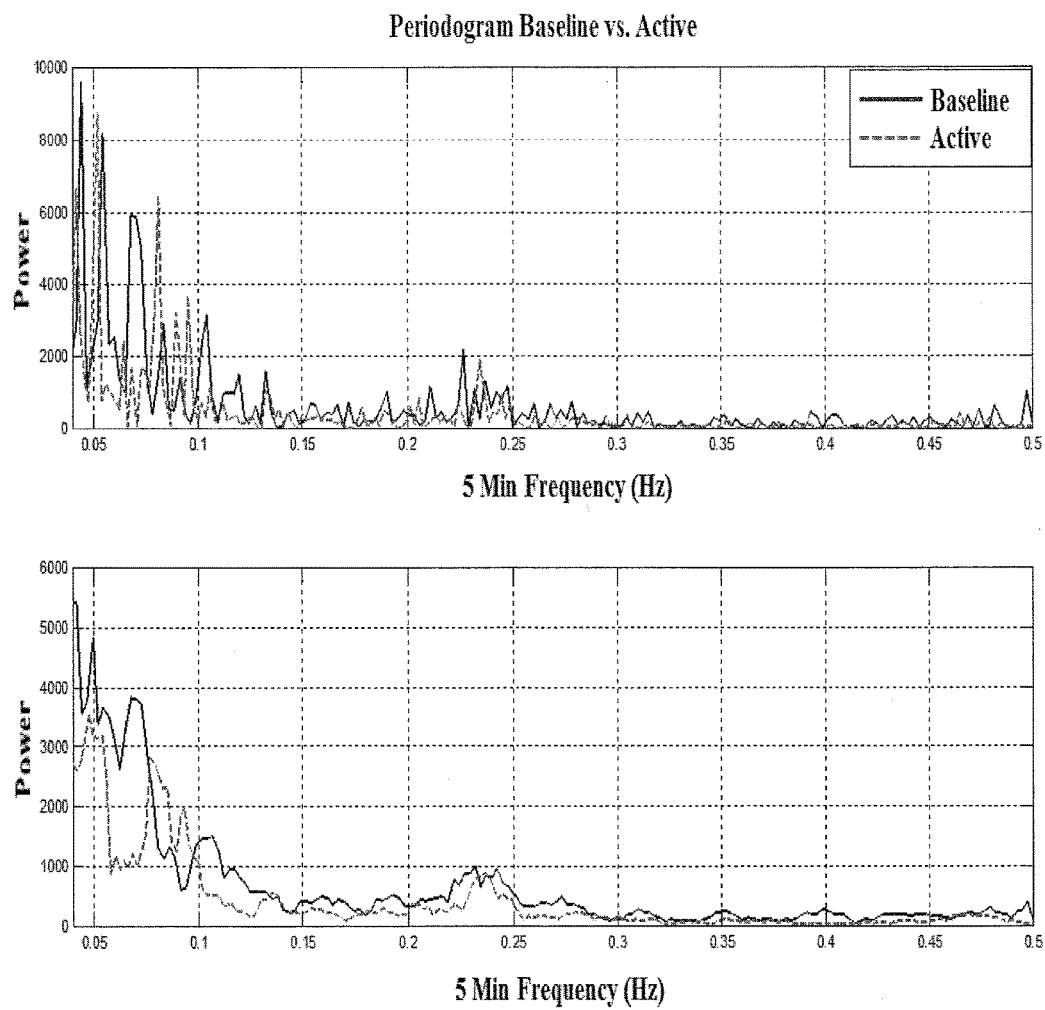
FIG. 7 is a power spectrum of an ECG signal comparing baseline to active phase.

FIG. 7 is a power spectrum of an ECG signal comparing baseline to active phase. Referring to FIG. 7, an illustration on a representative subject shows some differences in HRV (as determined from spectral analysis: LF and HF). These types of results were observed for all subjects of the study. The sampling rate of the ECG was 1 Hz, so the frequency spectrum was plotted until 0.5 HZ only, satisfying the Nyquist frequency criteria. As can be observed, the power spectrum of the ECG shows a significant change in the power around 0.05 Hz and 0.1 Hz during the stimulation using 10 Hz and 5 repetitions. Repetitive TMS, particularly after stimulation of the left hemisphere, induced a slight decrease in the parasympathetic (HF components of the spectrum) and an evident decrease on the sympathetic activity (LF power spectrum).

Figure 8:
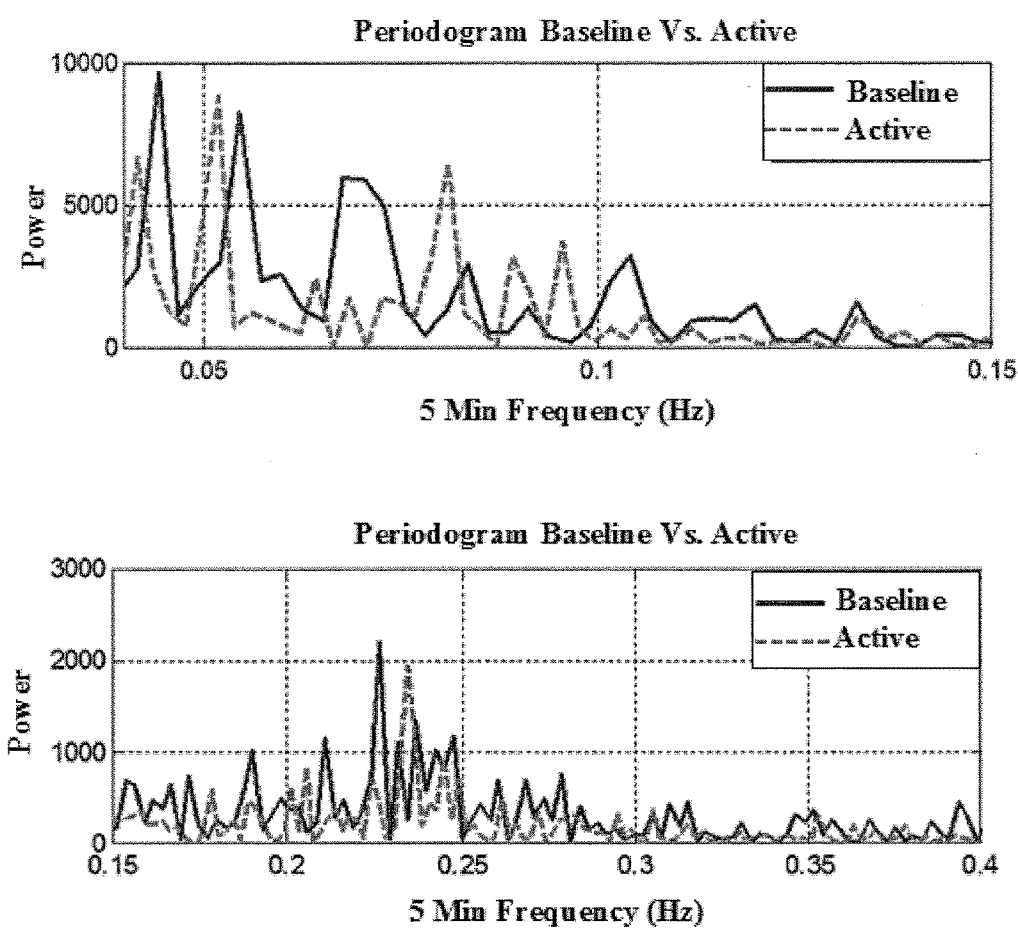
FIG. 8 is a power spectrum contrasting low frequency components (left) and high frequency components (right) at baseline and during the active phase.

FIG. 8 is a power spectrum contrasting low frequency components (left) and high frequency components (right) at baseline and during the active phase. Referring to FIG. 8, a comparison of the area under the curve (AUC) of the low frequency (LF) and high frequency (HF) components was also performed to the RR intervals during 5 minutes (baseline and magnetic stimulation) for one of the subjects as an illustrative example. Calculations of the areas under the power spectrum in FIG. 8 indicate a drop in the area of the active phase of over 35% on the average with respect to the area of the baseline for both the high and low frequency components.

FIG. 9 is an illustration of observed changes on RR intervals for two subjects: subject 1 (top row); and subject 2 (bottom row). FIG. 9 expresses these changes using a different modality by showing a comparison of the RR intervals between baseline (supine position during 5 minutes) and the activation phase (during rTMS using 10 Hz).

Referring to FIG. 9, the slopes of the baseline (blue; the line that is on the top at the left side of each plot) and active (red; the line that is on the bottom at the left side of each plot) RR intervals are calculated for each minute during the recording to show the effect of the rTMS in the heart rate. There were 5 stimulations applied at the beginning of each minute until 5 minutes. The stimulation started at the beginning of every minute and lasted only 1 second. The effects of the magnetic stimulation were observed for 59 seconds, until stimulation (1 second) began. It can be observed that there is an evident deflection of the RR intervals from the baseline. During stimulation, heart rate increased due to a decrease of the RR interval values.

Referring again to FIG. 6, the gradual move of the red segments (active phase; bottom left portion of the plot) towards the blue (baseline; top right portion of the plot) segments in time as stimulations are given. It is possible that in time the effect of the stimulation on the ECG is lessened, though this is not necessarily the case.

It is important to know and understand the basic interactions between the human cortex and the autonomic nervous system. ECG monitoring when stimulating patients through the TMS machine is advantageous, especially in subjects with known heart ailments or for persons in older age groups. This is essential for checking in real-time for any potential changes that could lead to unforeseen events. Embodiments of the subject invention can stop stimulation automatically as soon as such initial changes occur. For example, it is reported that subjects older than 40 years of age are more vulnerable to alterations of the cardiac rhythm. If any rTMS session should be undertaken, a monitoring ECG protocol should be followed in order to avoid any further complications.

In addition, monitoring of the HRV is a powerful tool for better understanding the cardiovascular system. Because rTMS has a great impact on some patients suffering from a diverse number of neurological diseases, it remains to be determined if it can help to predict any cardiac condition during or after any session of a repetitive magnetic stimulation.

All patents, patent applications, provisional applications, and publications referred to or cited herein (including those in the "References" section) are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

1. Prikryl, Radovan; Ustohal, Libor; Kucerova, Hana Prikrylova; et al. "Repetitive transcranial magnetic stimulation reduces cigarette consumption in schizophrenia patients", Progress in Neuro-Psychopharmacology & Biological Psychiatry, Vol. 49, pp. 30-35, March 2014.
2. Levkovitz, Yechiel; Rabany, Liron; Harel, Eiran Vadim; et al., "Deep transcranial magnetic stimulation add-on for treatment of negative symptoms and cognitive deficits of schizophrenia: a feasibility study", Intl. Journal of Neuropsychopharmacology, Vol. 14 (7), pp. 991-996, August 2011.
3. Plewnia, Christian; Pasqualetti, Patrizio; Grosse, Stephan; et al. "Treatment of major depression with bilateral theta burst stimulation: A randomized controlled pilot trial", Journal of Affective Disorders, Vol. 156, pp. 219-223, March 2014.
4. Herwig, U; Lampe, Y; Juengling, F D; et al, "Add-on rTMS for treatment of depression: a pilot study using stereotaxic coil-navigation according to PET data", Journal of Psychiatric Research, Vol. 37 (4), pp. 267-275, July-August 2003.
5. Harel, Eiran Vadim; Zangen, Abraham; Roth, Yiftach; et al., "H-coil repetitive transcranial magnetic stimulation for the treatment of bipolar depression: an add-on, safety and feasibility study", World Journal of Biological Psychiatry, Vol. 12 (2), pp. 119-126, March 2011.
6. Bloch, Y.; Harel, E. V.; Aviram, S.; et al., "Positive effects of repetitive transcranial magnetic stimulation on attention in ADHD Subjects: A randomized controlled pilot study", World Journal of Biological Psychiatry Vol. 11 (5), pp. 755-758, August 2010.
7. Acosta, M T; Leon-Sarmiento, F E, "Repetitive transcranial magnetic stimulation (rTMS): new tool, new therapy and new hope for ADHD", Current Medical Research and Opinion Vol. 19 (2), pp. 125-130, 2003.
8. Fregni, F; Santos, C M; Myczkowski, M L; et al., "Repetitive transcranial magnetic stimulation is as effective as fluoxetine in the treatment of depression in patients with Parkinson's disease", Journal of Neurology Neurosurgery and Psychiatry, Vol. 75 (8), pp. 1171-1174, August 2004.
9. Bauer, Prisca R.; Kalitzin, Stiliyan; Zijlmans, Maeike; et al., "Cortical excitability as a potential clinical marker of epilepsy: a review of the clinical application of transcranial magnetic stimulation", International Journal of Neural Systems, Vol. 24(2), March 2014.
10. Julkunen, Petro; Jauhiainen, Anne M.; Western-Punnonen, Susanna; et al, "Navigated TMS combined with EEG in mild cognitive impairment and Alzheimer's disease: A pilot study", Journal of Neuroscience Methods, Vol. 172 (2), pp. 270-276, July 2008.
11. Rossini, Paolo M.; Rossi, Simone; Babiloni, Claudio; et al, "Clinical neurophysiology of aging brain: From normal aging to neurodegeneration", Progress in Neurobiology, Vol. 83 (6), pp. 375-400, December 2007.
12. Sokhadze, Estate M.; El-Baz, Ayman; Baruth, Joshua; et al, "Effects of Low Frequency Repetitive Transcranial Magnetic Stimulation (rTMS) on Gamma Frequency Oscillations and Event-Related Potentials During Processing of Illusory Figures in Autism", Journal of Autism and Developmental Disorders, Vol. 39 (4), pp. 619-634, April 2009.
13. Philpott, April L.; Fitzgerald, Paul B.; Cummins, Tarrant D. R.; et al., "Transcranial magnetic stimulation as a tool for understanding neurophysiology in Huntington's disease: A review", Neuroscience and Biobehavioral Reviews, Vol. 37 (8), pp. 1420-1433, September 2013.
14. Bastani, A.; Jaberzadeh, S., "Does anodal transcranial direct current stimulation enhance excitability of the motor cortex and motor function in healthy individuals and subjects with stroke: A systematic review and meta-analysis", Clinical Neurophysiology, Vol. 123(4), pp. 644-657, April 2012.
15. Siebner, Hartwig R.; Hartwigsen, Gesa; Kassuba, Tanja; et al, "How does transcranial magnetic stimulation modify neuronal activity in the brain? Implications for studies of cognition", CORTEX, Vol. 45 (9), pp. 1035-1042, October 2009
16. Bolognini, Nadia; Pascual-Leone, Alvaro; Fregni, Felipe, "Using non-invasive brain stimulation to augment motor training-induced plasticity", Journal of Neuroengineering and Rehabilitation, Vol. 6, March 2009.
17. Manganotti, Paolo; Formaggio, Errianuela; Storti, Silvia Francesca; et al., "Effect of High-Frequency Repetitive Transcranial Magnetic Stimulation on Brain Excitability in Severely Brain-Injured Patients in Minimally Conscious or Vegetative State", Brain Stimulation, Vol. 6 (6), pp. 913-921, November, 2013.
18. Peters, Judith C; Reithler, Joel; Schuhmann, Teresa; et al, "On the feasibility of concurrent human TMS-EEG-fMRI measurements", Journal oF Neurophysiology Vol. 109 (4) pp. 1214-1227, February 2013.
19. Pellicciari, Maria Concetta; Brignani, Debora; Miniussi, Carlo, "Excitability modulation of the motor system induced by transcranial direct current stimulation: A multimodal approach", NeuroImage Vol. 83, pp. 569-580, December 2013.
20. Pascual-Leone, Alvaro; Freitas, Catarina; Oberman, Lindsay; et al., "Characterizing Brain Cortical Plasticity and Network Dynamics Across the Age-Span in Health and Disease with TMS-EEG and TMS-fMRI", Brain Topography Vol. 24 (3-4), pp. 302-315, October 2011.
21. Frantseva, Marina; Cui, Jie; Farzan, Faranak; et al. Disrupted Cortical Conductivity in Schizophrenia: TMS-EEG Study", Cerebral Cortex, Vol. 24 (1), pp. 211-221, January 2014.
22. Wassermann, E M, Risk and safety of repetitive transcranial magnetic stimulation: report and suggested guidelines from the international workshop on the safety of repetitive transcranial magnetic stimulation, Jun. 5-7, 1996, Evoked Potentials-Electro encephalography and Clinical Neurophysiology, Vol. 108 (1), pp. 1-16, January 1998.
23. Rossi, Simone; Hallett, Mark; Rossini, Paolo M.; et al, "Safety, ethical considerations, and application guidelines for the use of transcranial magnetic stimulation in clinical practice and research", Clinical Neurophysiology Vol. 120 (12), pp. 2008-2039, December 2009
24. Hallett, M, "Transcranial magnetic stimulation and the human brain", Nature, Vol. 406 (6792), pp. 147-150, July 2000.
25. Rossini, Paolo M.; Rossi, Simone, "Transcranial magnetic stimulation—Diagnostic, therapeutic, and research potential", Neurology, Vol. 68 (7), pp. 484-488, February 2007.
26. Udupa K, Sathyaprabha T N, Thirthalli J, Kishore K R, Raju T R, Gangadhar B N. Modulation of cardiac autonomic functions in patients with major depression treated with repetitive transcranial magnetic stimulation. J Affect Disord. (2007); 104:231-6.
27. Yoshida T, Yoshino A, Kobayashi Y, Inoue M, Kamakura K, Nomura S. Effects of slow repetitive transcranial magnetic stimulation on heart rate variability according to power spectrum analysis. J Neurol Sci. (2001); 184:77-80.
28. Kamath M V, Fallen E L. Power spectral analysis of heart rate variability: a noninvasive signature of cardiac autonomic function. Crit Rev Biomed Eng. 1993; 21 (3): 245-311.

What is claimed is:

1. A system, comprising:
a hardware component comprising an integrated circuit;
a software component stored on a computer-readable medium and in operable communication with the hardware component: and
a Transcranial Magnetic Stimulation (TMS) machine capable of producing magnetic stimulation,
the integrated circuit being in operable communication the TMS machine,
the software component being configured to receive waveforms from electrocardiography (ECG) hardware and to compute a determination factor based on the received waveforms such that if the determination factor is outside a predetermined range, the software component sends an abort signal to the TMS machine to cease any magnetic stimulation,
the software component being further configured to accept an input from a user and to send a control signal to the hardware component to perform an operation on the TMS machine based on the input from the user,
the software component comprising a graphical user interface with which the user interacts to provide the input,
the TMS machine comprising a first pedal corresponding to aborting magnetic stimulation, a second pedal corresponding to decreasing intensity of a magnetic pulse, a third pedal corresponding to triggering a magnetic pulse with a predefined intensity, and a fourth pedal corresponding to increasing intensity of a magnetic pulse,
the hardware component further comprising a first solenoid disposed adjacent to the first pedal of the TMS machine,
the system being configured such that, if the user input indicates that magnetic stimulation is to be aborted the hardware component presses the first pedal of the TMS machine by activating the first solenoid, and
the system being configured such that detection of a highest peak of an R wave by the ECG hardware is synchronized with triggering of the TMS machine.

2. The system according to claim 1, wherein the operation performed on the TMS machine based on the input from the user is at least one of the following: abort magnetic stimulation; increase intensity of a magnetic pulse; decrease intensity of a magnetic pulse; or trigger a magnetic pulse with a predefined intensity.

3. The system according to claim 1, wherein, if the determination factor is outside the predetermined range, sending the abort signal to the TMS machine comprises the software component sending a control signal to the hardware component such that the hardware component presses the first pedal of the TMS machine by activating the first solenoid.

4. The system according to claim 1, wherein the hardware component further comprises a second solenoid disposed adjacent to the second pedal of the TMS machine, a third solenoid disposed adjacent to the third pedal of the TMS machine, and a fourth solenoid disposed adjacent to the fourth pedal of the TMS machine, wherein the hardware component is configured to press at least one of the second pedal, the third pedal, and the fourth pedal of the TMS machine by activating the second solenoid, the third solenoid, and the fourth solenoid, respectively, and
wherein the system is configured such that:
if the user input indicates a decrease in the intensity of a magnetic pulse, the hardware component presses the second pedal of the TMS machine by activating the second solenoid;
if the user input indicates a triggering of a magnetic pulse with a predefined intensity, the hardware component presses the third pedal of the TMS machine by activating the third solenoid; and if the user input indicates an increase in the intensity of a magnetic pulse, the hardware component presses the fourth pedal of the TMS machine by activating the fourth solenoid.

5. The system according to claim 1, wherein the determination factor is an RR interval of a PQRST waveform.

6. The system according to claim 1, wherein the predetermined range is a baseline range of a patient hooked up to the ECG hardware, plus a variability factor extending each endpoint of the baseline range, and
wherein the variability factor is based on the patient and is determined by the user.

7. The system according to claim 6, wherein the variability factor is 10%.

8. The system according to claim 1, wherein the integrated circuit is in operable communication with the ECG hardware, and
wherein the software component receives the waveforms from the ECG hardware via the hardware component.

9. A method for controlling magnetic stimulation to a patient, comprising:
determining a current state of a patient's heart based on at least one waveform received from ECG hardware hooked up to the patient; and
synchronizing control of magnetic stimulation to the patient based on a determination factor of the current heart state and detection of a highest peak of an R wave detected by the ECG hardware,
the synchronizing control of the magnetic stimulation to the patient being performed using a system, the system comprising:
a hardware component comprising an integrated circuit;
a software component stored on a computer-readable medium and in operable communication with the hardware component; and
a Transcranial Magnetic Stimulation (TMS) machine capable of producing magnetic stimulation,
the integrated circuit being in operable communication with the TMS machine,
the synchronizing control of magnetic stimulation to the patient comprising providing a control signal to control generation of or level of magnetic stimulation provided by the TMS machine,
the software component being configured to receive the at least one waveform from the ECG hardware and to compute the determination factor of the current heart state based on the at least one waveform and, if the determination factor is outside a predetermined range, the software component sends an abort signal to the TMS machine to cease any magnetic stimulation,
the software component being configured to accept an input from a user and to send a control signal to the hardware component to perform an operation on the TMS machine based on the input from the user, the operation being at least one of the following: abort magnetic stimulation; increase intensity of a magnetic pulse; decrease intensity of a magnetic pulse; and trigger a magnetic pulse with a predetermined intensity,
the software component comprising a graphical user interface with which the user interacts to provide the input,
the TMS machine comprising a first pedal corresponding to aborting magnetic stimulation, a second pedal corresponding to decreasing intensity of a magnetic pulse, a third pedal corresponding to triggering a magnetic pulse with a predefined intensity, and a fourth pedal corresponding to increasing intensity of a magnetic pulse,
the hardware component further comprising a first solenoid disposed adjacent to the first pedal of the TMS machine, and
the system being configured such that, if the user input indicates that magnetic stimulation is to be aborted, the hardware component presses the first pedal if the TMS machine by activating the first solenoid.

10. The method according to claim 9, wherein the hardware component further comprises a second solenoid disposed adjacent to the second pedal of the TMS machine, a third solenoid disposed adjacent to the third pedal of the TMS machine, and a fourth solenoid disposed adjacent to the fourth pedal of the TMS machine, wherein the hardware component is configured to press at least one of the second pedal, the third pedal, and the fourth pedal of the TMS machine by activating the second solenoid, the third solenoid, and the fourth solenoid, respectively, and
wherein the system is configured such that:
if the user input indicates a decrease in the intensity of a magnetic pulse, the hardware component presses the second pedal of the TMS machine by activating the second solenoid;
if the user input indicates a triggering of a magnetic pulse with a predefined intensity, the hardware component presses the third pedal of the TMS machine by activating the third solenoid; and
if the user input indicates an increase in the intensity of a magnetic pulse, the hardware component presses the fourth pedal of the TMS machine by activating the fourth solenoid.

11. The method according to claim 9, wherein the determination factor is an RR interval of a PQRST waveform.

12. The method according to claim 9, wherein the predetermined range is a baseline range of the patient, plus a variability factor extending each endpoint of the baseline range, and
wherein the variability factor is based on the patient and is determined by a user of the system.

* * * * *